(12) United States Patent
Rieger et al.

(10) Patent No.: US 11,304,651 B2
(45) Date of Patent: Apr. 19, 2022

(54) SYSTEMS AND METHODS FOR DIAGNOSIS AND TREATMENT OF SWALLOWING DISORDERS

(71) Applicants: The Governors of the University of Alberta, Edmonton (CA); Covenant Health, Edmonton (CA)

(72) Inventors: Jana Maureen Rieger, Edmonton (CA); Gabriela Constantinescu, Edmonton (CA); Mark James Redmond, Edmonton (CA); Dylan Kyle Scott, St. Albert (CA); Benjamin Ronald King, Beaumont (CA); Mark Vernon Fedorak, Edmonton (CA); Herman Lundgren, Gothenburg (SE)

(73) Assignees: THE GOVERNORS OF THE UNIVERSITY OF ALBERTA, Edmonton (CA); COVENANT HEALTH, Edmonton (CA)

( * ) Notice: Subject to any disclaimer, the term of this patent is extended or adjusted under 35 U.S.C. 154(b) by 454 days.

(21) Appl. No.: 15/313,892

(22) PCT Filed: May 22, 2015

(86) PCT No.: PCT/CA2015/000342
§ 371 (c)(1),
(2) Date: Nov. 23, 2016

(87) PCT Pub. No.: WO2015/179950
PCT Pub. Date: Dec. 3, 2015

(65) Prior Publication Data
US 2017/0188934 A1 Jul. 6, 2017

Related U.S. Application Data

(60) Provisional application No. 62/002,833, filed on May 24, 2014.

(51) Int. Cl.
*A61B 7/00* (2006.01)
*G16H 20/30* (2018.01)
(Continued)

(52) U.S. Cl.
CPC .......... *A61B 5/4205* (2013.01); *A61B 5/0022* (2013.01); *A61B 5/22* (2013.01);
(Continued)

(58) Field of Classification Search
CPC ..... A61B 5/4205; A61B 5/228; A61B 5/6814; A61B 5/7225; A61B 5/0022; A61B 7/006;
(Continued)

(56) References Cited

U.S. PATENT DOCUMENTS

| 8,147,407 B2 | 4/2012 | Moore et al. |
| 2002/0133194 A1* | 9/2002 | Leelamanit ........ A61N 1/36014 607/2 |

(Continued)

FOREIGN PATENT DOCUMENTS

| KR | 20120139479 A | 12/2012 |
| WO | 2012101514 A2 | 8/2012 |

OTHER PUBLICATIONS

International Search Report dated Sep. 10, 2015 in International Application No. PCT/CA2015/000342, 3 pages.
(Continued)

*Primary Examiner* — Rene T Towa
(74) *Attorney, Agent, or Firm* — Norton Rose Fulbright Canada LLP

(57) ABSTRACT

A system is provided for monitoring patients with dysphagia, or swallowing impairments, that monitors muscle movement during intensive swallowing exercises to provide adjuvant visual feedback from surface electromyography.

31 Claims, 13 Drawing Sheets

(51) Int. Cl.
 A61B 5/389 (2021.01)
 A61B 5/22 (2006.01)
 A61B 5/00 (2006.01)
 G16H 40/63 (2018.01)
(52) U.S. Cl.
 CPC .............. *A61B 5/228* (2013.01); *A61B 5/389* (2021.01); *A61B 5/6814* (2013.01); *A61B 5/7225* (2013.01); *A61B 7/006* (2013.01); *G16H 20/30* (2018.01); *A61B 5/42* (2013.01); *A61B 5/4833* (2013.01); *A61B 5/6822* (2013.01); *A61B 2560/0223* (2013.01); *G16H 40/63* (2018.01)
(58) Field of Classification Search
 CPC ....... A61B 5/22; A61B 5/0488; A61B 5/4833; A61B 5/6822; A61B 5/42; A61B 2560/0223; G06Q 50/24; G06F 19/00; G06F 19/3418; G06F 19/34; G16H 40/63
 See application file for complete search history.

(56) References Cited

U.S. PATENT DOCUMENTS

| | | | |
|---|---|---|---|
| 2004/0082877 A1 | 4/2004 | Kouou et al. | |
| 2005/0049517 A1* | 3/2005 | Mathew | A61B 5/389 600/546 |
| 2006/0064037 A1* | 3/2006 | Shalon | A61B 5/0006 600/586 |
| 2007/0282228 A1* | 12/2007 | Einav | A61B 5/16 601/33 |
| 2009/0030346 A1* | 1/2009 | Kojima | A61B 5/11 600/590 |
| 2010/0210935 A1* | 8/2010 | Woodward | A61B 5/0492 600/391 |
| 2012/0190959 A1* | 7/2012 | Hayakawa | A61B 5/0478 600/383 |
| 2012/0209089 A1* | 8/2012 | Garde | A61B 5/103 600/301 |
| 2012/0245492 A1* | 9/2012 | Lee | A61B 5/1114 600/595 |
| 2013/0289434 A1 | 10/2013 | Chou et al. | |
| 2013/0310661 A1* | 11/2013 | Jedwab | A61B 5/1107 600/301 |
| 2014/0106642 A1* | 4/2014 | Irmler | A63G 31/00 446/338 |
| 2014/0303459 A1* | 10/2014 | Wada | A61B 5/0402 600/301 |
| 2016/0136516 A1* | 5/2016 | Hooke | A63F 9/24 463/34 |

OTHER PUBLICATIONS

Lee, J. et al., "Swallow segmentation with artificial neural networks and multi-sensor fusion", Medical Engineering & Physics, Butterworth-Heinemann, GB, vol. 31, No. 9, Jul. 30, 2009, pp. 1049-1055, XP026734261.

Constantinescu Gabriela et al., "Mobili-T: A Mobile Swallowing-Therapy Device: An Interdisciplinary Solution for Patients with Chronic Dysphagia", 2014 IEEE 27th International Symposium on Computer-Based Medical Systems, IEEE, May 27, 2014, pp. 431-434, XP032629487.

Supplementary European Search Report, completed Mar. 16, 2018, issued in corresponding European Application No. EP 15799129, 8 pages.

* cited by examiner

SYSTEMS AND METHODS FOR DIAGNOSIS AND TREATMENT OF SWALLOWING DISORDERS

CROSS-REFERENCE TO RELATED APPLICATIONS

This is a national stage of PCT/CA2015/000342, filed May 22, 2015, which claims priority to U.S. provisional patent application Ser. No. 62/002,833 filed May 24, 2014, which are incorporated by reference into this application in its their entirety.

TECHNICAL FIELD

This disclosure relates to systems and methods for diagnosing and treating swallowing disorders also known as dysphagia and more particularly to providing a device that may be used to diagnose and treat swallowing disorders.

BACKGROUND

Swallowing disorders (e.g., dysphagia) are serious medical conditions that have detrimental effects to the mental and physical well-being of individuals. Swallowing impairments can lead to serious health problems, such as malnutrition and aspiration pneumonia, as well as psychosocial concerns and poor quality of life.

Limited clinical capacity and service-delivery models that require clinician-supervised therapy imply that patients receive potentially sub-optimal treatment or, even worse, no treatment at all. Furthermore, this limited access to swallowing therapy has resulted in literature scarcity concerning the relative effectiveness of alternative therapies and the treatment dose necessary for clinically significant improvements.

Dysphagia (i.e., difficulty swallowing) affects two in ten Canadians over the age of 50. Patients with a swallowing impairment often are unable to consume a normal diet, which can lead to dependence or semi-dependence on tube feeding. This alteration in eating affects social interactions, and overall quality of life. The distress and social isolation can lead some patients to risk eating foods unsafe for them to swallow. For some patients, a swallowing impairment can be so serious that it results in significant weight loss and muscle wasting. Furthermore, swallowing impairments are commonly associated with pneumonia because food and oral secretions go down the wrong way and into the lungs. Pneumonia is a costly condition to treat and can result in death.

Swallowing therapy, especially that using surface electromyography ("sEMG") for feedback about what the swallowing muscles are doing, can improve oral intake, reduce aspiration of food into the lungs, and eliminate the need for a feeding tube. Typical swallowing rehabilitation is based on theories of intensive exercise programs that target specific muscular structures and sequences of physiologically-based movements, and sEMG biofeedback has been used to monitor muscle activation during therapy as well as to train more complex treatment techniques. One exercise that has been coupled with sEMG biofeedback, the Mendelsohn maneuver, involves the volitional prolongation of a swallow, addressing laryngeal elevation and cricopharyngeal opening. When using sEMG biofeedback with the Mendelsohn maneuver, clinicians can set signal-amplitude goals (targeting muscle activation and force) and signal-duration goals (targeting duration of muscle contraction). While sEMG has been the main technology used for biofeedback in swallowing disorders, another technology, mechanomyography ("MMG"), may be a viable alternative to sEMG. In some embodiments, MMG can make use of a sensor capable of measuring mechanical oscillations originating from muscle contractions to sense muscle contractions. It some embodiments, such sensors can comprise a microphone. MMG has been used as a measurement technique for many physiotherapy applications that monitor the contraction of large muscle groups in the legs or arms. While reports in the literature are few to support its use for swallowing, those that do exist suggest that MMG may be sensitive enough to monitor movement in small muscles groups such as those in the submental area that contract during swallowing.

More than a decade ago, sEMG biofeedback technologies for treating swallowing disorders were brought into the clinical mainstream when KayPentax™, a leading developer of speech and swallowing therapy instrumentation, introduced a clinician friendly version. Since that time, the KayPentax™ system has been used both as a clinical and research sEMG tool. However, the system costs may make it inaccessible to many clinical units. Furthermore, it is not transportable to a patient's home and only works with the packaged computer and operating system.

In addition to using the KayPentax™ system, speech pathologists involved in sEMG swallowing research have either devised their own hardware or found other options, such as the Sys/3 4-channel computer-based EMG system from NeuroDyne™ Medical, Cambridge™, MAIM or ADInstruments™. ADInstruments™ provides a wireless system (PowerLab™ hardware and LabChart™ software), which is used to record and analyze sEMG signals. This technology, although wireless, is still costly and requires training to set up and use. The sensors themselves are larger than the sEMG adhesive pad used with the KayPentax™ system described above (37 mm×26 mm×15 mm) and weigh 14.7 g. Although these systems may be more cost-effective than the KayPentax™ system, it is unlikely that the typical speech-language pathologist has access to biomedical engineers who can provide the necessary engineering and computer-programming support for these systems to be functional. Therefore, few options remain for the typical clinician.

Dr. Catriona Steele, speech pathologist in the Swallowing Rehabilitation Research Laboratory at the Toronto Rehabilitation Institute, has tried to meet the need for inexpensive alternatives by developing software (BioGraph Infiniti™ Thought Technology™, Montreal) that can be paired with existing sEMG hardware (MyoTrac Infiniti™, Thought Technology™, Montreal). The device is still relatively large (61 mm×112 mm×25 mm) and weighs 71 g. Further, in order to use this equipment, clinicians are encouraged to take a fee-based course through the Biofeedback Foundation of Europe, which leads them through a standardized swallow treatment protocol progressing from regular swallow tasks to those involving the Mendelsohn Maneuver. Although this option may provide clinicians with a more cost-effective option, it does not address concerns related to accessibility of treatment, especially in the home environment with an engaging interface. Furthermore, the current technologies produce highly complex data that are not meaningful to the patient, affecting their motivation and engagement. Finally, data output for the clinician is not automated, requiring manual translation of data points.

Thus, swallowing therapy with the use of sEMG may be scarce due to the cost of the existing equipment, lack of equipment portability and taxed clinician availability. Furthermore, swallowing treatment occurring at a clinic does not happen as often as it should because: 1) there are not enough clinicians to meet the demand; 2) current treatment technology is costly and not readily available in many clinics; and 3) many patients live in remote areas, limiting access to major rehabilitation centers. In the current Albertan population, approximately 1.1 million people are over the age of 50, meaning that more than 220,000 Albertans are affected by a swallowing disorder. Unfortunately, the current workforce of just over 1,000 speech-language pathologists in Alberta is not sufficient to treat this population using conventional rehabilitation. On top of the aging population, patients prefer to remain home as much as possible, or simply cannot travel to treatment centers, calling for remote provision of treatment and management of chronic health issues, such as dysphagia.

In addition to the systems described above, Dysphagia iOS™ Applications are currently available. iSwallow™ and Swallow Now™ are iOS™ applications intended to be used by patients outside a clinic. iSwallow™ allows the clinician to create a personalized treatment regimen by selecting from a set of swallowing exercises. While the application provides patients with video instructions for various swallowing exercises, it is not coupled with sEMG biofeedback. One problem with eHealth applications (and more generally, at-home regimens), such as iSwallow™, is adherence; namely, accurately recording the patient's commitment to the regime and/or use of the application at home. Patient adherence to a treatment regimen is an important factor in improving health outcomes, but simply tracking patient activity does not ensure, or even motivate, adherence. The example devices described herein may use game concepts and design principles to motivate patients to use maximal effort in practice and to adhere to the complete treatment regimen.

It is, therefore, desirable to provide a system that overcomes the shortcomings of the prior art.

SUMMARY

In general, this disclosure describes a system for use in diagnosing and treating swallowing disorders. In particular, this disclosure describes providing a device to an individual, wherein the device is configured to provide visual feedback to the individual. In some examples, the device may include a mobile device, for example, a smart phone. In one example, the techniques can be implemented as part of a mobile device application.

The details of one or more examples are set forth in the accompanying drawings and the description below. Other features, objects, and advantages will be apparent from the description and drawings, and from the claims.

Broadly stated, in some embodiments, a system can be provided for use in the diagnosis and treatment of a swallowing disorder of a patient, the system comprising: a computing device; and a measurement device configured for attaching to the patient, wherein the measurement device is configured to transmit surface electromyography ("sEMG") or mechanomyography ("MMG") data to the computing device.

Broadly stated, in some embodiments, the measurement device can further comprise a chin attachment configured for attachment to a chin of the patient.

Broadly stated, in some embodiments, the system can further comprise a wearable computing device.

Broadly stated, in some embodiments, the system can further comprise a housing configured for attachment to a chin of the patient, wherein the measurement device and the wearable computing device are disposed in the housing.

Broadly stated, in some embodiments, the wearable computing device can be configured for amplifying and filtering a sEMG signal derived from the sEMG data or a MMG signal derived from the MMG data.

Broadly stated, in some embodiments, the wearable computing device can be configured for transmitting the sEMG or MMG signal to the computing device.

Broadly stated, in some embodiments, the computing device can comprise one or more processors configured for: receiving the sEMG signal or the MMG signal; and generating a graphical user interface based on the received sEMG or MMG signal.

Broadly stated, in some embodiments, the graphical user interface can be configured for indicating the duration of submental muscle contraction in the patient.

Broadly stated, in some embodiments, the computing device can comprise one or more processors configured for calculating an average and a range signal amplitude of the sEMG or MMG signal during a calibration phase.

Broadly stated, in some embodiments, the computing device can comprise one or more processors configured for determining one or more of a group consisting of: time of log-in, duration of session, length of time since last session, session's target amplitude, type of exercise practiced, number of trials, amplitude for each trial, duration for each trial, average for each type of exercise, duration average for each type of exercise, and range for each type of exercise.

Broadly stated, in some embodiments, a method can be provided for use in the diagnosis and treatment of a swallowing disorder of a patient, the method comprising the steps of: providing the system described above; attaching the measurement device described above to a chin of the patient; and measuring muscle contraction of the patient when the patient swallows.

Broadly stated, in some embodiments, the method can further comprise the step of providing audible or visual feedback to the patient, wherein the feedback provides an indication of the muscle contraction to the patient.

DETAILED DESCRIPTION

In general, this disclosure describes a system for use in diagnosing and treating swallowing disorders.

In some embodiments, the devices described herein, unlike current in-clinic technology, can be portable and relatively inexpensive and can allow a patient to complete therapy at home, and can allow a clinician to monitor a patient's activity remotely through access to a data warehouse and/or an online portal. Further, in some embodiments, unlike current technology, applications described herein can provide meaningful feedback to a patient about what their swallowing muscles are doing. This can be done by incorporating game concepts and design, such as goal setting, patient position relative to goal, creation and personalization, connections and ways to share results, practice reminders and progress bars into the application. In some embodiments, de-identified home practice data can be sent instantaneously to a central server so that the clinician can monitor progress and change the course of therapy. In addition, uploaded data can be used to create an evidence-base for this type of treatment that will ultimately guide clinical decision-making. Further, in one example, devices described herein can incorporate feedback from additional clinicians outside the core clinical or research group, as well as patients and health administrators. The mobile health devices described herein can be used to: improve quality of life in patients with swallowing difficulties by providing more consistent, motivating and accessible swallowing therapy; address an unmet clinical need in the health system; and provide an effective technological solution to reduce the burden of costs on patients, and the health care system.

Figure 1A:
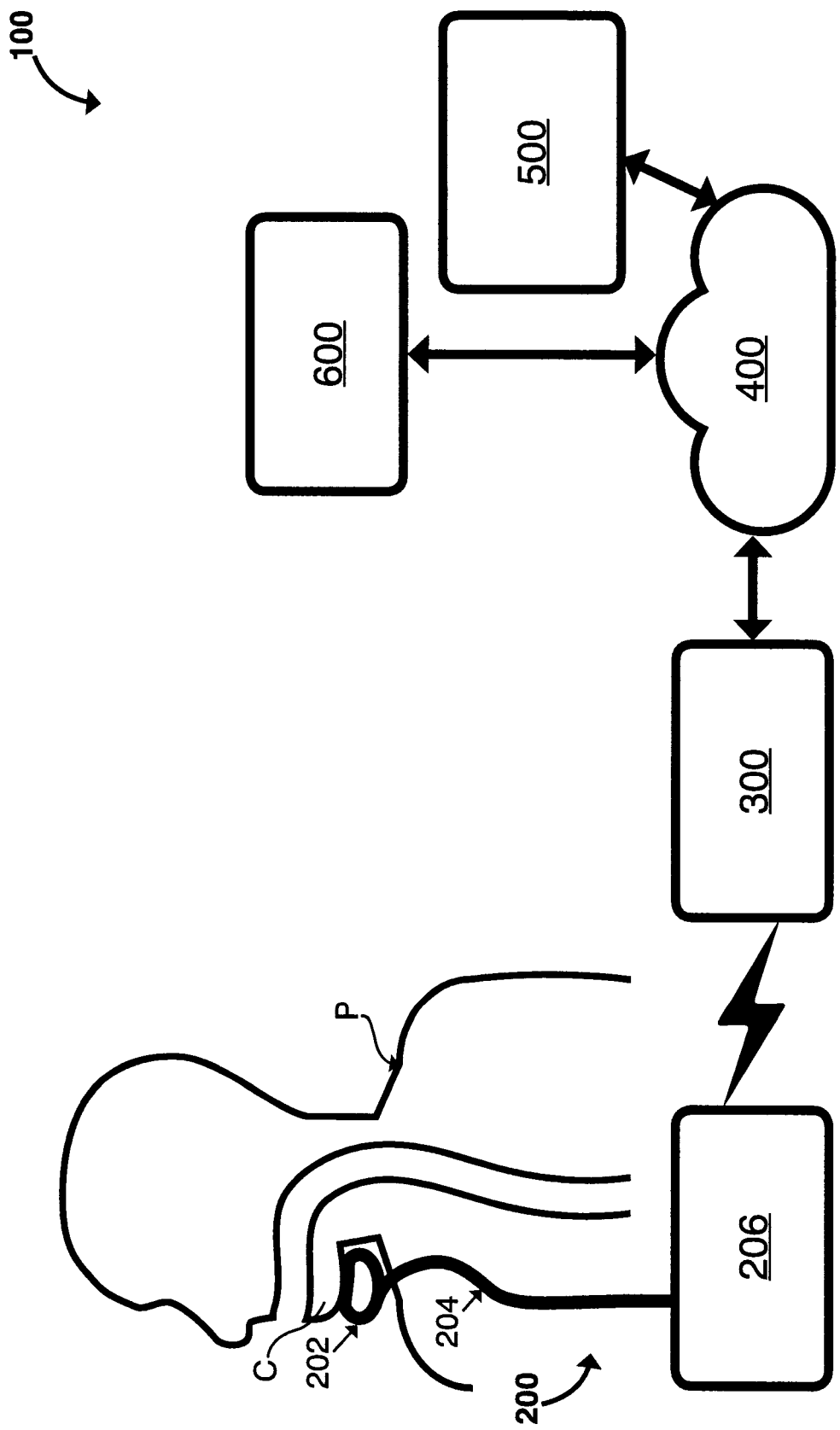
FIG. 1A is a block diagram depicting one embodiment of a system used for the diagnosis and treatment of swallowing disorders in which the sensor and wearable computing device are separated and connected by a cable.
Figure 1B:
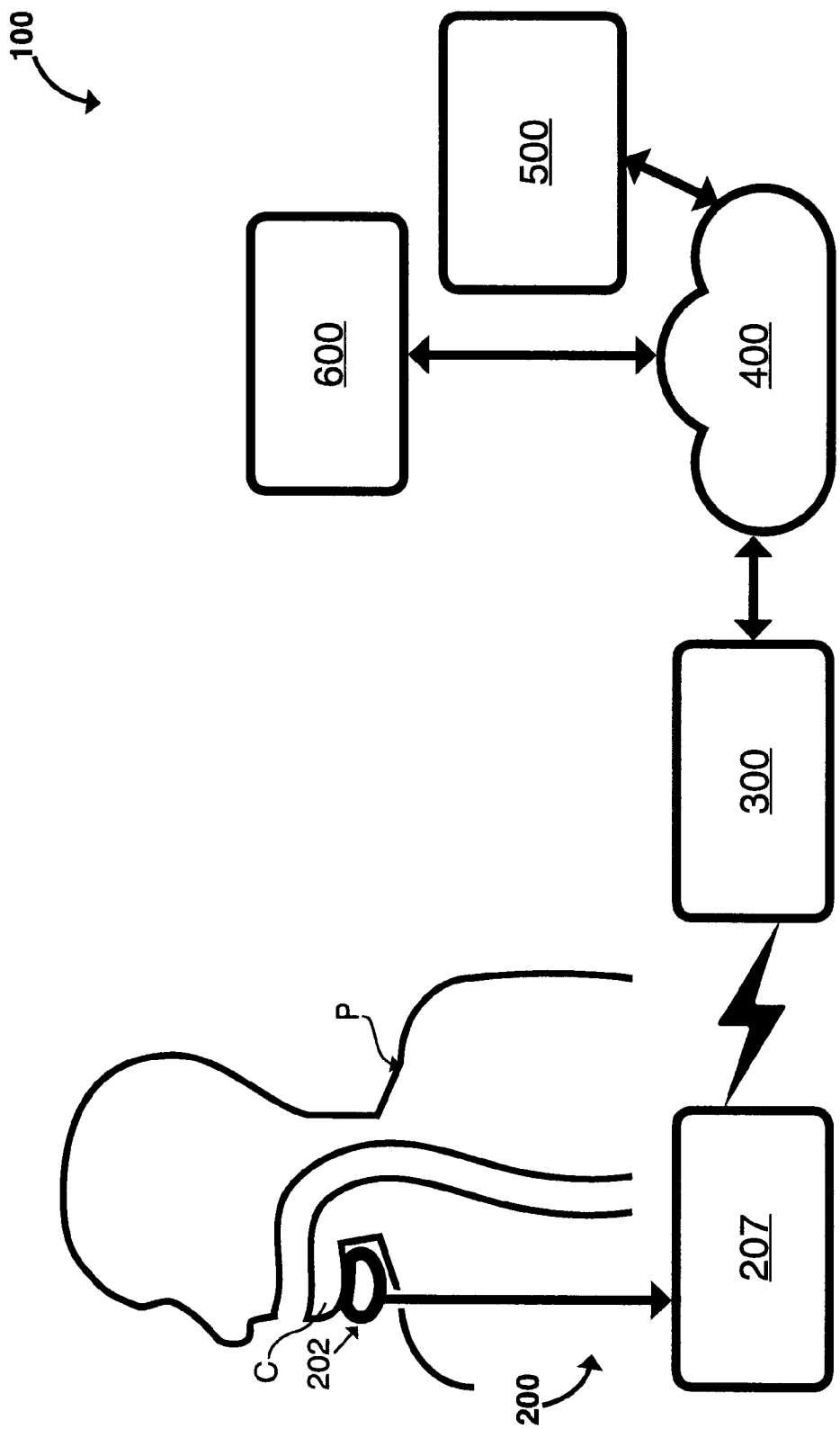
FIG. 1B is a block diagram depicting another embodiment of the system of FIG. 1A in which the sensor and wearable computing device are enclosed in the same housing.

FIG. 1A and FIG. 1B are block diagrams illustrating embodiments of systems that can implement one or more techniques of this disclosure. System 100 can be configured to treat and diagnose swallowing disorders in accordance with the techniques described herein. System 100 can be configured to observe the sEMG or MMG signal of patients practicing the Mendelsohn maneuver or other swallowing exercises and through an associated mobile application motivate, record and analyze individual trials and sessions and provide feedback to the patient. In some embodiments, the application can comprise a game. In the embodiment illustrated in FIG. 1A, system 100 can comprise measurement device 200, computing device 300, communications network 400, data warehouse and clinician portal 500 and clinical site 600.

Components of system 100 can comprise and be implemented as any of a variety of suitable hardware and software, such as one or more microprocessors, microcontrollers, digital signal processors ("DSPs"), application specific integrated circuits ("ASICs"), field programmable gate arrays ("FPGAs"), discrete logic, analog circuitry, software, software modules, hardware, firmware or any combinations thereof as well known to those skilled in the art. System 100 can comprise software modules operating on one or more servers. Software modules can be stored in a memory and executed by a processor. Servers can comprise one or more processors and a plurality of internal and/or external memory devices. Examples of memory devices can comprise file servers, FTP servers, network attached storage ("NAS") devices, a local disk drive or any other type of device or storage medium capable of storing data as well known to those skilled in the art. Storage medium can comprise Blu-ray discs, DVDs, CD-ROMs, flash memory or any other suitable digital storage media as well known to those skilled in the art. When the techniques described herein are implemented partially in software, a device can store instructions for the software in a suitable, non-transitory computer-readable medium and execute the instructions in hardware using one or more processors.

In some embodiments as illustrated in FIG. 1A, measurement device 200 can comprise chin attachment sensor 202 and a wearable computing device 206, where chin attachment sensor 202 and wearable computing device 206 can be electronically coupled. In some embodiments, a wire can be enclosed in rubber wiring enclosure 204 disposed between sensor 202 and device 206. In some embodiments, the length of the wire between chin attachment sensor 202 and wearable computing device 206 can be as short as possible to reduce signal noise while still allowing some slack for movement. Rubber material encasing the wires can be chosen to protect the wires and prevent unnecessary bending or fraying. In some embodiments as illustrated in FIG. 1B, measurement device 200 can have both the chin attachment sensor 202 and wearable computing device 207 contained in the same enclosure so as to remove the requirement for rubber wiring enclosure 204.

Figure 2A:
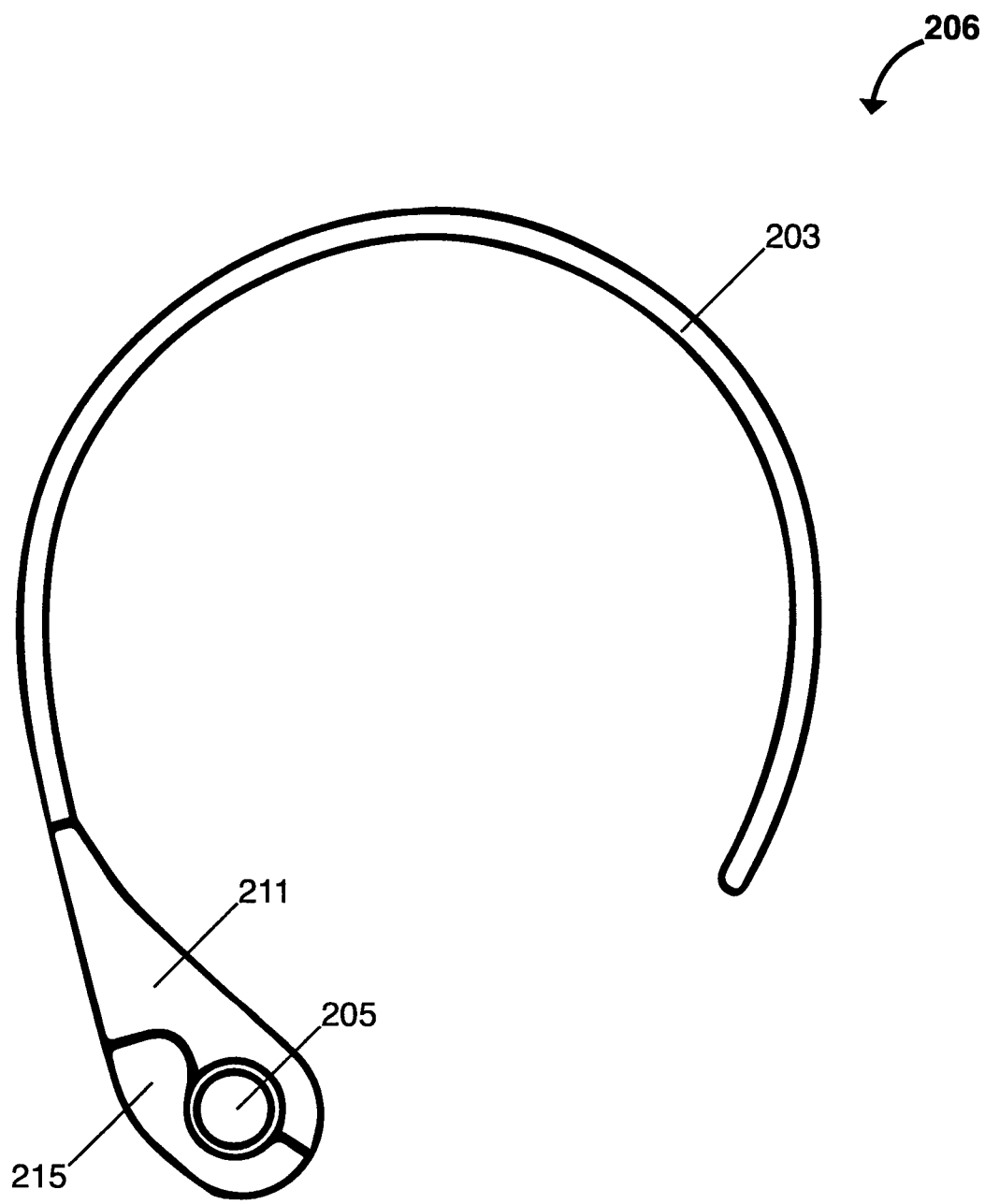
FIG. 2A is a top plan view depicting a wearable computing device for use with the system of FIG. 1A.
Figure 2B:
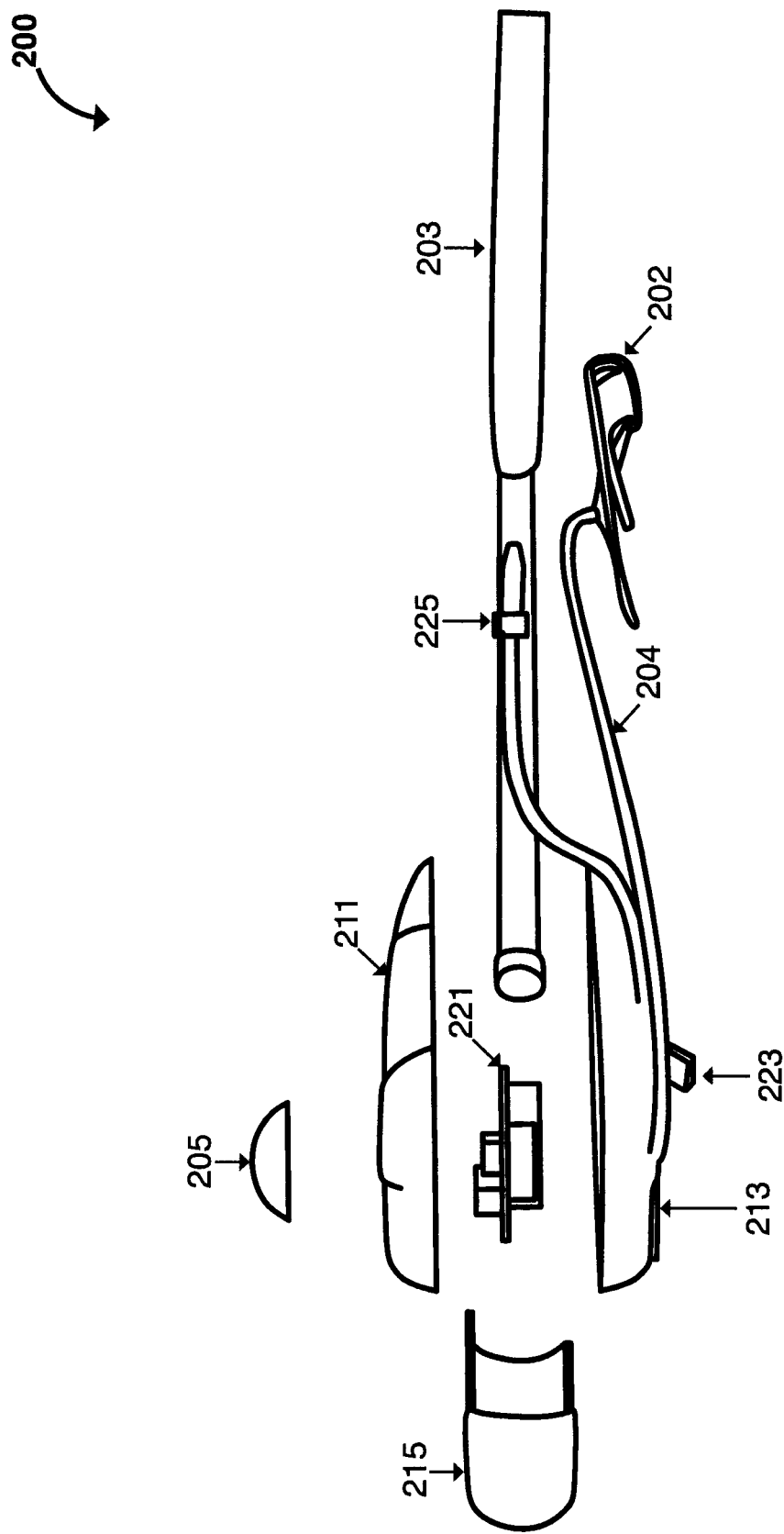
FIG. 2B is an exploded elevation view depicting the wearable computing device of FIG. 2A.
Figure 3A:
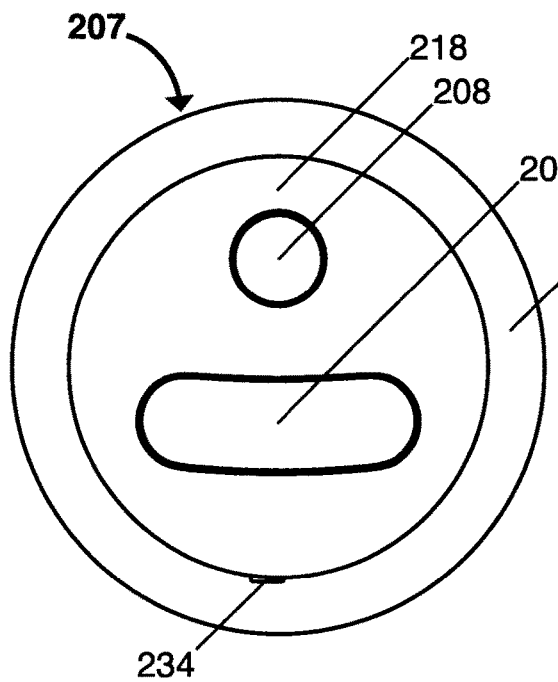
FIG. 3A is a top plan view depicting a wearable computing device use with the system of FIG. 1B.
Figure 3B:
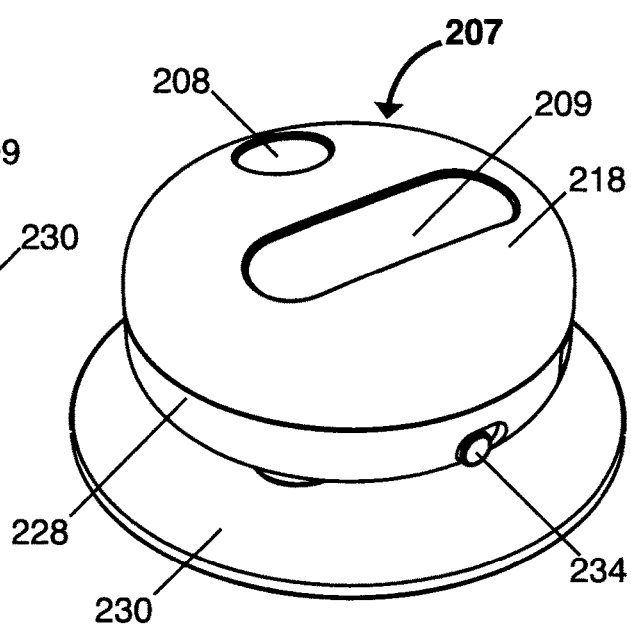
FIG. 3B is a perspective view depicting the wearable computing device of FIG. 3A.
Figure 3C:
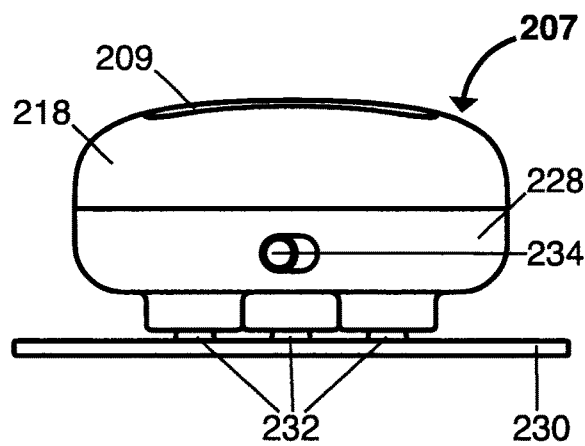
FIG. 3C is a front elevation view depicting the wearable computing device of FIG. 3A.
Figure 3D:
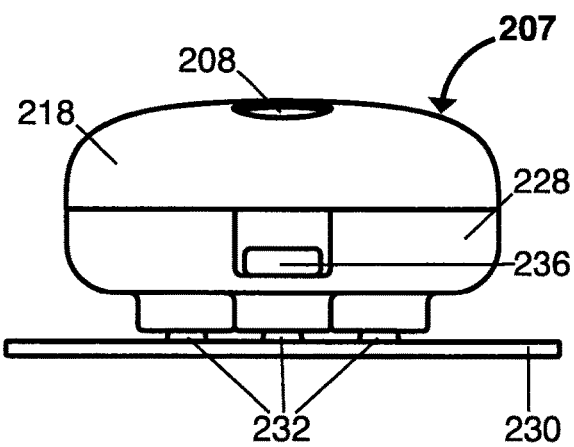
FIG. 3D is a rear elevation view depicting the wearable computing device of FIG. 3A.

FIGS. 2A and 2B illustrate one embodiment of wearable computing device 206 that can be used with system 100 as shown in FIG. 1A. In this embodiment, device 206 can be designed to accommodate users with limited shoulder range of motion, i.e., the neck-piece may be flexible and not require an overhead arm motion. In some embodiments, device 206 can comprise collar 203 further comprise casing halves 211 and 213 disposed on an end thereof. Casing halves 211 and 213 can enclose printed circuit board 221 disposed therein, where printed circuit board 221 can comprise the electronics and functionality, as described in further detail below. In some embodiments, casing halves 211 and 213 can be easily separated for repairs as necessary. Device 206 can further comprise silicone hand grip 215 configured to releasably attach to casing halves 211 and 213 when assembled together. In some embodiments, device 206 can comprise USB 223 connector disposed on casing half 213 and operatively connected to printed circuit board 221 for connecting to an external computing device (not shown). Device 206 can also comprise connector jack 225 operatively connected to printed circuit board 221 for providing a connection between chin attachment 202 and printed circuit board 221. Device 206 can also comprise chin attachment 202 configured to house a sEMG sensor or a MMG sensor and to attach to the chin of a patient, wherein chin attachment sensor 202 is operatively connected to printed circuit board 221 via electrical wires or cables disposed in rubber wiring enclosure 204 disposed between casing half 213 and chin attachment 202. In some embodiments, chin attachment 202 can be a universal fit device or can be custom-fitted to the patient.

Figure 4:
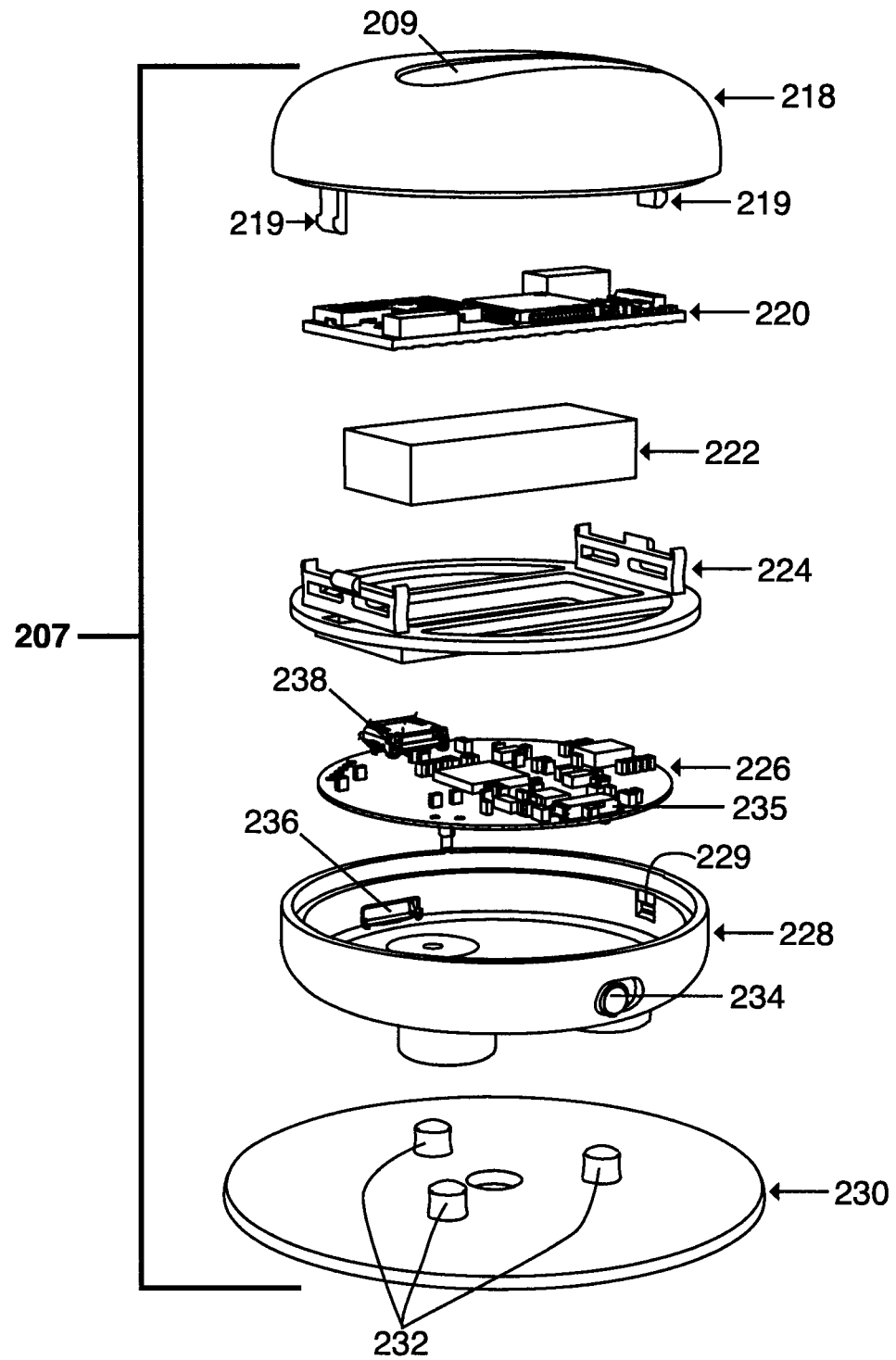
FIG. 4 is an exploded perspective view depicting the wearable computing device of FIG. 3A.

FIGS. 3A to 3D and 4 illustrate one embodiment of wearable computing device 207 that can be used with system 100 as shown in FIG. 1B. In this embodiment, sensor 202 and wearable computing device 206 can be included in the same enclosure to form device 207. As shown in FIG. 4, the casing for device 207 was designed to be mindful of the challenge that patients might have in aligning the device under the chin. In some embodiments, device 207 can comprise one or both of distinct recesses 208 and 209, each recess relating to the location of potential sEMG electrodes disposed in device 207. In some embodiments, singular circular recess 208 can be aligned vertically with a reference electrode, while longer rounded recess 209 can be vertically aligned with two active electrodes. This embodiment can provide both a visual and a tactile reference for proper alignment with the required anatomy. Other considerations from the patient's perspective involved referencing human factors measurements to ensure the device is appropriate for a variety of hand sizes, grip strengths and motor skills.

In some embodiments, device 207 can comprise top casing half 218, wireless transceiver module 220, battery 222 for providing electrical power to the electronics disposed in device 207, cradle 224 for housing battery 222 and module 220, printed circuit board 226, lower casing half 228 and sensor pad 230. In some embodiments, transceiver module 220 can be a Bluetooth™ transceiver. In some embodiments, casing half 218 can comprise tangs 219 to releasably attach to tang recesses 229 disposed in casing half 228 to enable easy disassembly of device 207 for repairs as necessary. In some embodiments, lower casing half 228 can comprise slidable button 234 to operate switch 235 disposed on circuit board 226 when installed in casing half 228. In some embodiments, lower casing half 228 can comprise opening 236 to provide access to electrical connector 238 disposed on circuit board 226 when installed in casing half 226. In some embodiments, sensor pad 230 can comprise electrodes 232 for connection to circuit board 226. In some embodiments, casing halves 218 and 228 can be approximately 50 mm in diameter, and can be comprised of materials that are easy to clean with hospital disinfectants, as well known to those skilled in the art.

In some embodiments, the enclosure can be designed to house battery 222, and circuit board 226 that can comprise charging circuitry, analog conditioning circuitry, connection to a plurality of electrodes 232 that can further comprise sEMG or MMG sensors, an onboard microcontroller unit, wireless transceiver module 220 that can comprise a wireless connection method such as, but not limited to, Bluetooth™ or Zigbee™, which can be all on one or more printed circuit board(s) 226. In some embodiments, the device can comprise all analog electronics necessary for signal acquisition and conditioning, as well as all digital electronics necessary for signal digitization and wireless data transfer. Some embodiments can comprise, located on the housing, a button or switch to turn the device off and on or indicate some other functionality to the internal electronics such as wake up or to change the current operational mode. In some embodiments, the device can comprise one or more indicators 216 which can comprise one or more of the following: light emitting diodes, a small screen, an audio indicator such as a speaker or piezo-electric indicator, a vibratory device and a haptic indicator, all of which can be used to indicate such things as whether the device is off or on, if it is charging or finished charging, if the wireless module is connected, battery charge level, if the device is taking a reading, as well as if the device is properly aligned on the individual.

Figure 5:
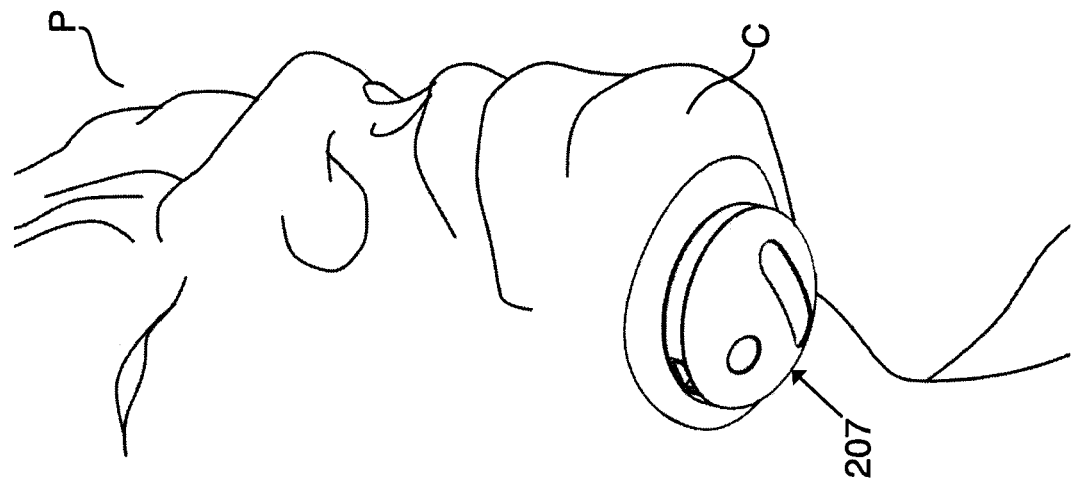
FIG. 5 is a perspective view depicting a patient wearing the wearable computing device of FIG. 3A.

Referring to FIG. 5, an embodiment of device 207 is shown attached to chin C of patient P, as an example.

Figure 6:
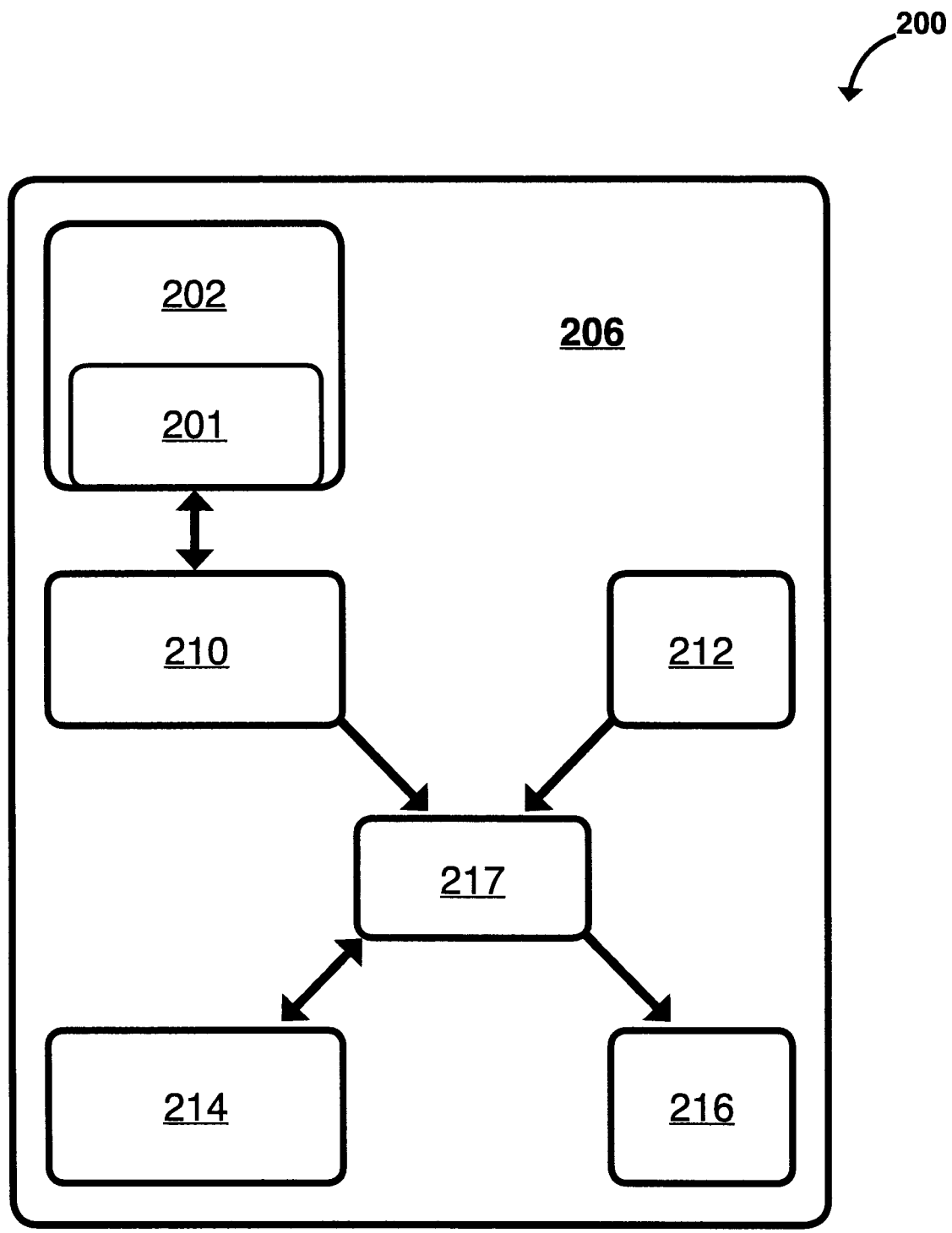
FIG. 6 is a block diagram depicting an embodiment of a wearable computing device for use with the system of FIG. 1A or FIG. 1B.

FIG. 6 is a block diagram illustrating an example measurement device 200 that can implement one or more techniques of this disclosure. Measurement device 200 can be configured to filter and amplify sEMG or MMG signals, and send those remotely to a mobile device, such as, for example, computing device 300. As illustrated in FIG. 6, in some embodiments, wearable computing device 206 can comprise includes chin attachment sensor 202, electrode(s) 201, signal processing module 210, microcontroller 217, power supply 212, wireless transceiver 214, and indicators 216. In some embodiments, electrode(s) 201 can comprise three electrodes. In other embodiments, electrode(s) 201 can be replaced with, or can further comprise, one or more MMG sensors. In some embodiments, electrodes can be coupled to sEMG adhesive pads. In one example, the sEMG adhesive pads can be light and inexpensive single-use pads that do not require cleaning, or they can comprise a medical-grade reusable solvent-based or non-solvent based adhesive or a silicon adhesive to provide for many uses before replacement. In other embodiments, the sEMG pads can all be included in the same adhesive pad to simplify the application. In other embodiments, this combined sensor pad can comprising one or more sEMG or MMG sensors can be connected to the enclosure, and then the enclosure and the sensors can be applied to the patient's chin together. In other embodiment, the sEMG pad can be coupled with a chin mold housing the leads. Further, the design of the chin mold can make the placement of the pad intuitive, and can further prevent incorrect connection of the adhesive pad to the leads. In some embodiments, an MMG sensor can comprise a MEMS microphone and an amplifying chamber created out of a biocompatible plastic or metal. The diameter of the chamber can have a diameter of approximately 7 mm and a height of approximately 10 mm. Further, aluminized Mylar™ can be used as the membrane (having 10 mm diameter) that can cross the amplifying chamber. In one example, power supply 212 can comprise a lithium battery. Further, power supply 212 can comprise USB port 238 or another custom connector to allow for the measuring device 200 to be charged. This port can also be used to move collected patient data off of the device, download new firmware into the device, and/or perform tests on the device. Alternatively, the device can be charged by induction through a wireless inductive link. The power supply 212 can also include circuitry to prevent the use of the system while the device is charging. Signal processing module 210 can be configured to capture and process a signal from electrodes. Wireless transceiver 214 can comprise a wireless transmitter that can communicate the captured signal to the mobile application for analysis. In one example, wireless transceiver 214 can comprise a Bluetooth™ transceiver and the transmitted data can comprise serial data. Indicators 216 can comprise one or more light emitting diodes to indicate an operating mode to a patient. In some embodiments, all of these components can be controlled by a firmware application running in microcontroller 217.

Figure 7A:
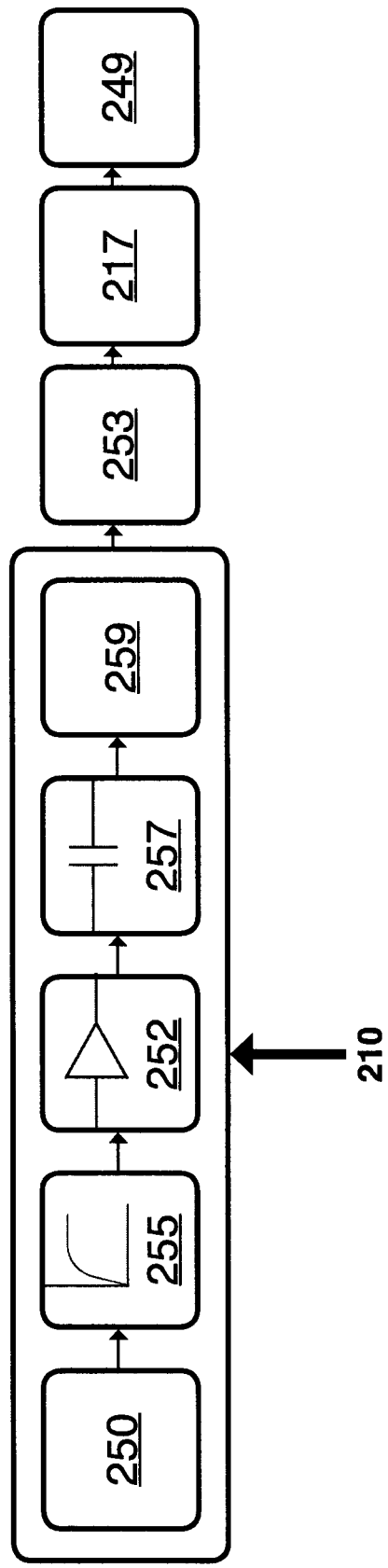
FIG. 7A is a block diagram depicting one embodiment of a sEMG signal processing module for use with the system of FIG. 1A or FIG. 1B.
Figure 7B:
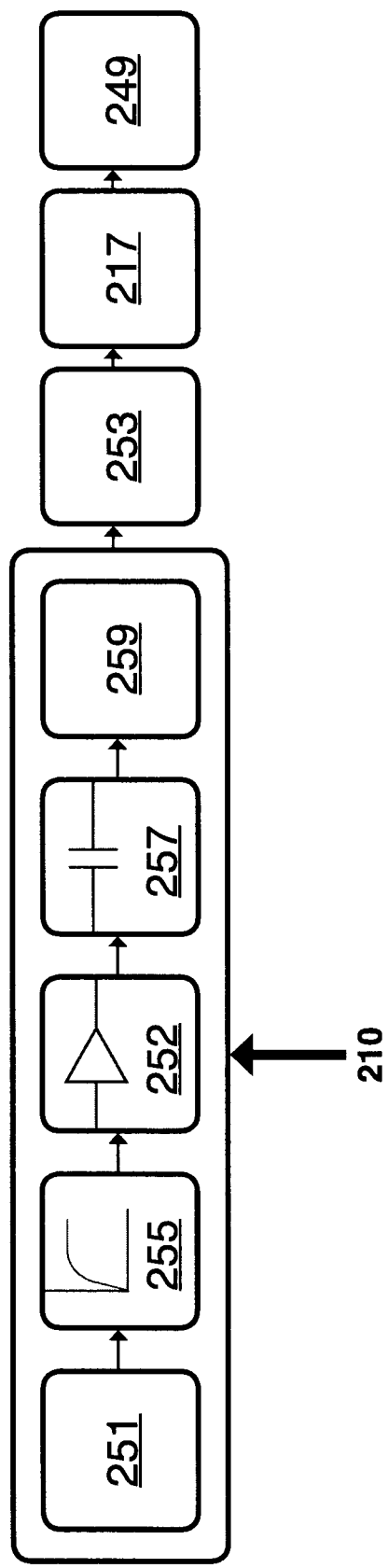
FIG. 7B is a block diagram depicting one embodiment of a MMG signal processing module for use with the system of FIG. 1A or FIG. 1B.
Figure 7C:
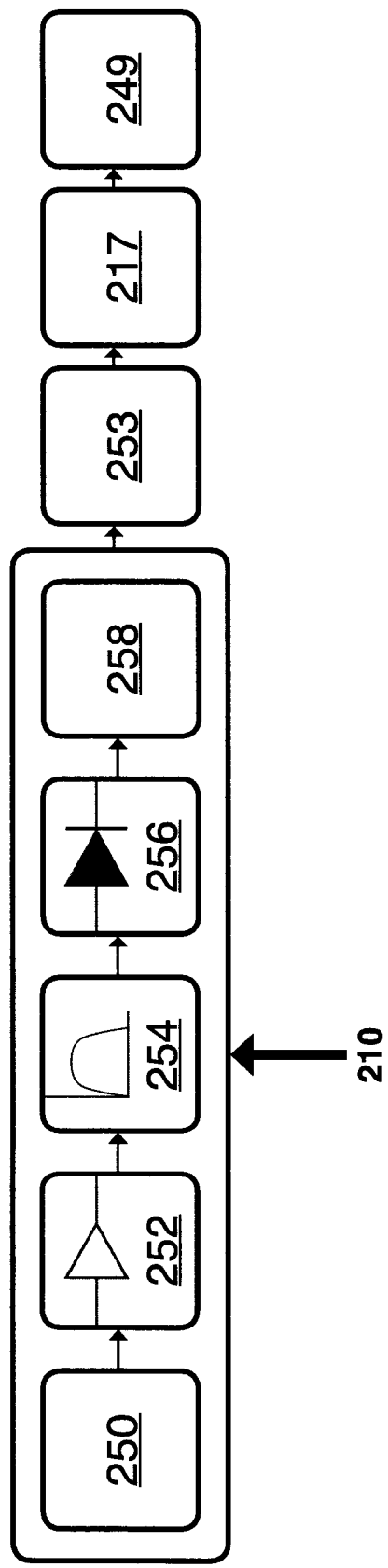
FIG. 7C is a block diagram depicting another embodiment of a sEMG signal processing module for use with the system of FIG. 1A or FIG. 1B.

FIG. 7C is a block diagram illustrating an example sEMG signal processing device that can implement one or more techniques of this disclosure. As illustrated in FIG. 7C, signal processing device 210 can comprise some or all of the following: signal acquisition module 250, amplification module 252, bandpass filter 254, rectification module 256 and envelope detection module 258. From signal processing device 210, the signal can be digitized by analog to digital converter 253, and then microcontroller 217 can send the digitized signal out through transmission interface module 249. In some embodiments, microcontroller 217 and analog to digital converter 253 can be disposed on the same integrated circuit.

FIG. 7A illustrates an alternative sEMG signal processing device 210 that can comprise only high pass filter 255 instead of bandpass filter 254, and can further comprise AC Coupling module 257 as well as DC Biasing module 259. In some embodiments, the output signal of signal processing device 210 can comprise a smoothed muscle response curve that is ready for digitization.

Figure 8:
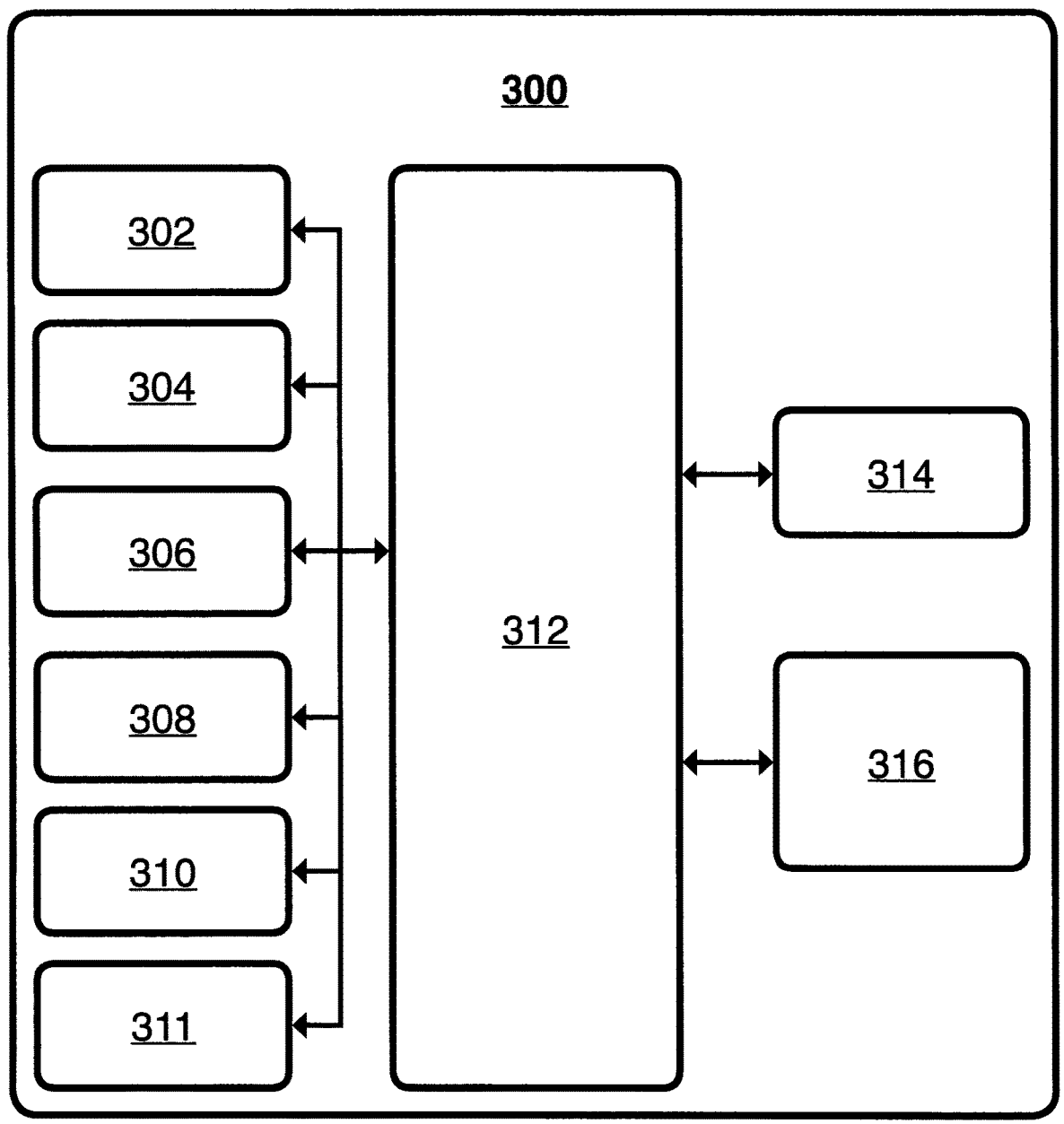
FIG. 8 is a block diagram depicting one embodiment of a computing device for use with the system of FIG. 1A or FIG. 1B.

FIG. 7B illustrates another embodiment of the system comprising MMG signal processing device 210, further comprising microphone 251 to gather the MMG signal. In some embodiments of device 210 as shown in FIGS. 7A and 7B, high pass filter 255 can comprise a cut-off frequency of 10 Hz. Referring back to FIG. 7C, in some embodiments, amplification module 252 can comprise an amplification factor of 1000. In some embodiments, bandpass filter 254 can comprise a 10 Hz to 500 Hz bandpass filter. In some embodiments, rectification module 256 can comprise a diode. In some embodiments, the amplification, filtering and rectification can be done via software on either measurement device 200 as shown in FIG. 6, or on computing device 300 as shown in FIG. 8. In some embodiments, the analysis and characterization of a swallow event of a patient can be done entirely on the measurement device 200, entirely on the computing device 300 or shared between both of these devices.

Referring again to FIG. 1A, in some embodiments, measurement device 200 can send sEMG signals to computing device 300; computing device 300 and clinical site 600 can be connected to data warehouse 500; and communications network 400 can comprise any combination of wireless and/or wired communication media as well known to those skilled in the art. In some embodiments, communication network 400 can comprise routers, switches, base stations or any other equipment well known to those skilled in the art that can facilitate communication between various devices and sites. In some embodiments, communication network 400 can form part of a packet-based network, such as a local area network, a wide-area network or a global network such as the Internet. In some embodiments, communication network 400 can operate according to one or more communication protocols, such as, for example, a Global System Mobile Communications ("GSM") standard, a long term evolution ("4G LTE") standard, a Worldwide Interoperability for Microwave Access ("WiMAX") standard, a Evolved High-Speed Packet Access ("HSPA+"), a code division multiple access ("CDMA") standard, a 3rd Generation Partnership Project ("3GPP") standard, an Internet Protocol ("IP") standard, a Wireless Application Protocol ("WAP") standard, and/or an IEEE standard, such as, one or more of the 802.11 standards, as well as various combinations thereof.

FIG. 8 is a block diagram illustrating one embodiment of computing device 300 that can implement one or more techniques of this disclosure. In some embodiments, computing device 300 can be configured to transmit data to and receive data from data warehouse 500 and execute one or more applications (for example, swallowing diagnosis and treatment application 316). In some embodiments, computing device 300 can comprise, or be part of, a portable computing device (e.g., a mobile phone, smart phone, netbook, laptop, personal data assistant ("PDA")), or tablet device or a stationary computer (e.g., a desktop computer, or set-top box or any other computing device as well known to those skilled in the art. In some embodiments, computing device 300 can comprise processor(s) 302, memory 304, input device(s) 306, output device(s) 308, network interface 310 and wireless transceiver 311. In some embodiments, each of processor(s) 302, memory 304, input device(s) 306, output device(s) 308, network interface 310 and wireless transceiver 311 can be interconnected (physically, communicatively, and/or operatively) for inter-component communications. In some embodiments, operating system 312, applications 314 and swallowing diagnosis and treatment application 316 can be executed by computing device 300. It should be noted that although computing device 300, as shown in FIG. 8, is illustrated as having distinct functional blocks, such this illustration is for descriptive purposes only, and does not limit computing device 300 to any particular hardware architecture. The functions of computing device 300 can be realized using any combination of hardware, firmware and/or software implementations as well known to those skilled in the art.

In some embodiments, processor(s) 302 can be configured to implement functionality and/or process instructions for execution in computing device 300. In some embodiments, processor(s) 302 can be capable of retrieving and processing instructions, code, and/or data structures for implementing one or more of the techniques described herein. Instructions can be stored on a computer readable medium, such as memory 304. In some embodiments, processor(s) 302 can comprise digital signal processors ("DSPs"), general purpose microprocessors, application specific integrated circuits ("ASICs"), field programmable logic arrays ("FPGAs") or other equivalent integrated or discrete logic circuitry as well known to those skilled in the art.

In some embodiments, memory 304 can be configured to store information that can be used by computing device 300 during operation. Memory 304 can comprise a non-transitory or tangible computer-readable storage medium. In some embodiments, memory 304 can provide temporary memory and/or long-term storage. In some embodiments, memory 304 or portion thereof can comprise volatile memory, that is, in some cases; memory 304 may not maintain stored contents when computing device 300 is powered down. Examples of volatile memories can include random access memories ("RAM"), dynamic random access memories ("DRAM") and static random access memories ("SRAM"). Memory 304 can be comprised as internal or external memory and, in some embodiments, can comprise non-volatile storage elements. Examples of such non-volatile storage elements can include magnetic hard discs, optical discs, floppy discs, flash memories, forms of electrically programmable memories ("EPROM") or electrically erasable and programmable ("EEPROM") memories and other non-volatile storage elements as well known to those skilled in the art.

In some embodiments, input device(s) 306 can be configured to receive input from user operating computing device 300. Input from a user can be generated as part of the user running one or more software applications, such as swallowing diagnosis and treatment application 316. In some embodiments, input device(s) 306 can comprise a touch-sensitive screen, a track pad, a track point, a mouse, a keyboard, a microphone, a video camera, or any other type of device configured to receive input from a user as well known to those skilled in the art.

In some embodiments, output device(s) 308 can be configured to provide output to user operating computing device 300. Output can comprise tactile, audio or visual output generated as part of a user running one or more software applications, such as swallowing diagnosis and treatment application 316. In some embodiments, output device(s) 308 can comprise a touch-sensitive screen, sound card, a video graphics adapter card or any other type of device for converting a signal into an appropriate form understandable to humans or machines as well known to those skilled in the art. Additional examples of output device(s) 308 can comprise a speaker, a cathode ray tube ("CRT") monitor, a liquid crystal display ("LCD") or any other type of device that can provide audio or visual output to a user as well known to those skilled in the art. In some embodiments where computing device 300 comprises a mobile device, output device(s) 308 can comprise an LCD or organic light emitting diode ("OLED") display configured to receive user touch inputs, such as, for example, taps, drags and pinches as well known to those skilled in the art.

In some embodiments, network interface 310 can be configured to enable computing device 300 to communicate with external devices via one or more networks, such as communications network 400. Network interface 310 can comprise a network interface card, such as an Ethernet card, an optical transceiver, a radio frequency transceiver or any other type of device that can send and receive information as well known to those skilled in the art. In some embodiments, network interface 310 can be configured to operate according to one or more of the communication protocols described above with respect to communications network 400. In some embodiments, network interface 310 can enable a patient computing device running swallowing diagnostic and treatment application 316 to transmit information to clinical site 600 or to data warehouse and online clinician portal 500. In some embodiments, clinical site 600 can comprise a server. In some embodiments, the data can be disposed in the data warehouse and online clinician portal 500 with the clinician at the clinical site 600 accessing a patient's data using a web browser through the World Wide Web. In some embodiments, wireless transceiver 311 can comprise a wireless transceiver configured to send and receive data to and/or from measurement device 200. In some embodiments, wireless transceiver 311 and network interface 310 can be integrated. In some embodiments, the data can be encrypted before transmission to clinical site 600 or to data warehouse and online clinician portal 500. This encryption can comprise use any number of different encryption technologies such as, but not limited to, Advance Encryption Standard ("AES"), Transport Layer Security ("TLS") or its predecessor, Secure Sockets Layer ("SSL"), RSA, Secure Shell ("SSH"), Data Encryption Standard ("DES") and any other equivalent encryption technology as well known to those skilled in the art. The encryption and decryption of data can be done by swallowing diagnostic and treatment application 316, by operating system 312 or by integrated circuits and processor(s) 302 at a hardware level that compose computing device 300.

In some embodiments, operating system 312 can be configured to facilitate the interaction of applications, such as applications 314 and swallowing diagnosis and treatment application 316, with processor(s) 302, memory 304, input device(s) 306, output device(s) 308, network interface 310, and wireless transceiver 311 of computing device 300. In some embodiments, operating system 312 can be an operating system designed to be installed on laptops and desktops. For example, operating system 312 can comprise a Windows™ operating system, Linux® or Mac OS™. In embodiments where computing device 300 comprises a mobile device, such as a smartphone or a tablet, operating system 312 can be one of Android™, iOS™ and Windows™ mobile operating system.

In some embodiments, applications 314 can comprise any applications implemented within or executed by computing device 300 and can be implemented or contained within, operable by, executed by, and/or be operatively/communicatively coupled to components of computing device 300. In some embodiments, applications 314 can comprise instructions that can cause processor(s) 302 of computing device 300 to perform particular functions. In some embodiments, applications 314 can comprise algorithms that are expressed in computer programming statements, such as: for loops, while-loops, if-statements, do-loops, etc. In some embodiments, applications can be developed using a programming language. Examples of programming languages can comprise Hypertext Markup Language ("HTML"), Dynamic HTML, Extensible Markup Language ("XML"), Extensible Stylesheet Language ("XSL"), Document Style Semantics and Specification Language ("DSSSL"), Cascading Style Sheets ("CSS"), Synchronized Multimedia Integration Language ("SMIL"), Wireless Markup Language ("WML"), Java™, Jini™, C, C++, Objective C, C #, PerI™, Python™, UNIX™ Shell, Visual Basic™ or Visual Basic™ Script, Virtual Reality Markup Language ("VRML") and ColdFusion™ as well as other compilers, assemblers and interpreters as well known to those skilled in the art.

Figure 9:
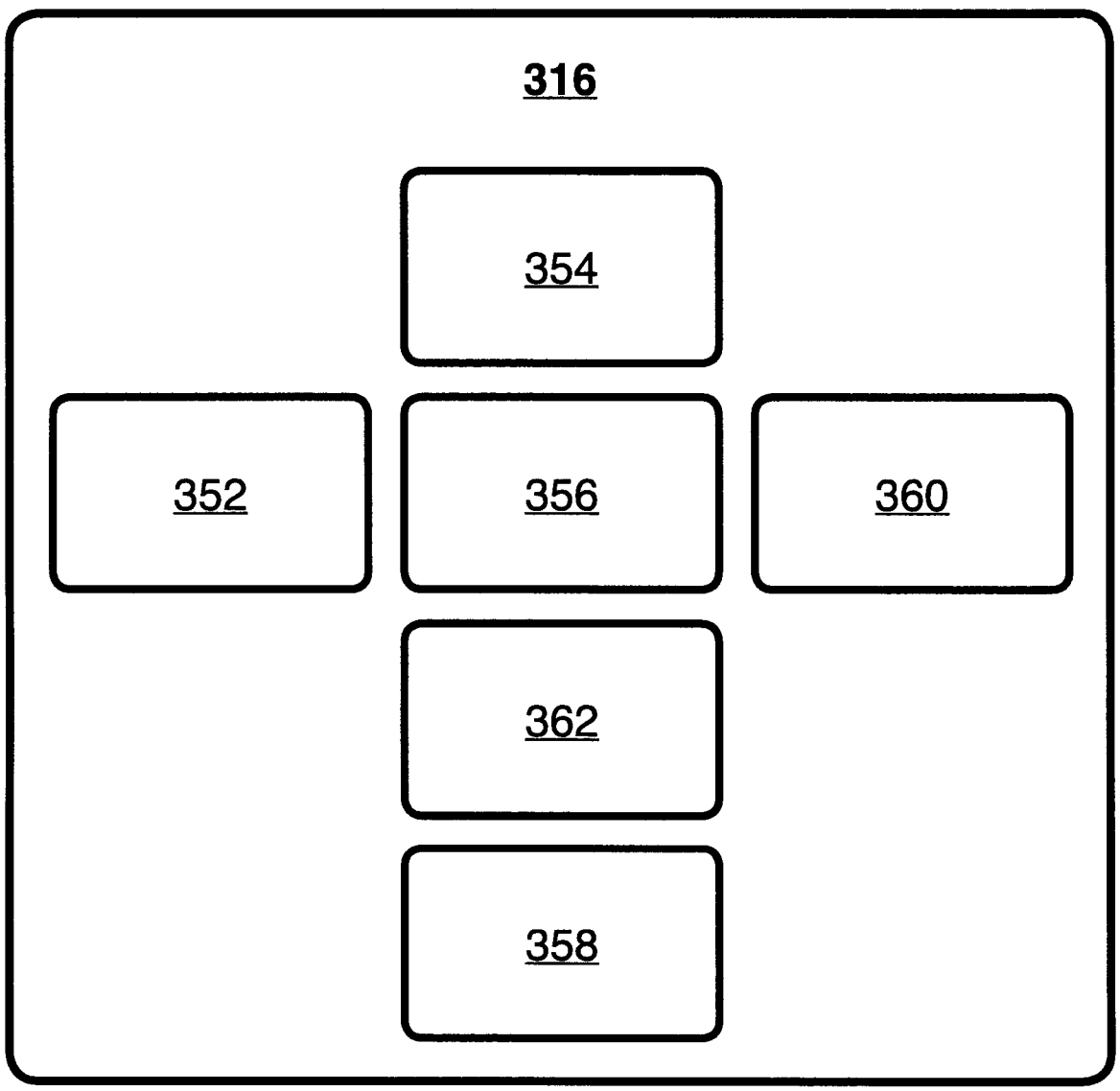
FIG. 9 is a block depicting one embodiment of applications for use with the computing device of FIG. 8.

In some embodiments, swallowing diagnosis and treatment application 316 can comprise an application configured to diagnose and treat a swallowing disorder according to the techniques described herein. FIG. 9 is a conceptual diagram illustrating an embodiment of swallowing diagnosis and treatment application 316. As illustrated in FIG. 8, swallowing diagnosis and treatment application 316 can comprise interface module 352, analysis module 362, training phase module 354, calibration module 356, game module 358 and transmission module 360. In some embodiments, these modules illustrated in FIG. 9 can comprise software modules and/or can be implemented using any combination of hardware, software or firmware as well known to those skilled in the art. In some embodiments, the modules illustrated in FIG. 9 can comprise software stored locally on computing device 300. In other embodiments, the modules illustrated in FIG. 9 can comprise software modules and/or portions thereof distributed throughout system 100.

FIG. 9 illustrates a conceptual diagram of an example operation of an application for treating and diagnosing a swallowing disorder in accordance with one or more techniques of this disclosure. In some embodiments, interface module 352 can be configured to generate graphical user interfaces. In some embodiments, training phase module 354 can be configured to achieve the functions associated with first visit training phase. In some embodiments, calibration module 356 can be configured to achieve the functions associated with warm-up and self-calibration phase. In some embodiments, the warm-up phase can tell the user if the sensor is applied incorrectly. In some embodiments, the self-calibration phase can record typical swallows for the patient on any one particular day and use this data to set a target exertion for the data. In some embodiments, analysis module 362 can analyze the real time data gathered from the patient to detect, using an algorithm, and various parameters for each swallowing exercise. In some embodiments, this algorithm can combine a number of analysis techniques in both the time and frequency domain to detect swallowing characteristics as well known to those skilled in the art. In some embodiments, game module 358 can be configured to use the outputs of analysis module 362 to achieve the functions associated with a game, and/or full training mode, and/or to display the signal to the patient as visual feedback.

In some embodiments, transmission module 360 can be configured to transmit data to either clinical site 600 or to data warehouse and online clinician portal 500. In some embodiments, anonymized or one way identifiable home practice data can be sent to a central server so that the clinician can monitor progress and change the course of therapy, if necessary. In some embodiments, one or more of the following metrics can be collected and saved at clinical site: (1) time of log-in; (2) duration of session; (3) length of time since last session; (4) session's target amplitude (μV); (5) type of exercise practiced and number of trials; (6) amplitude (μV) and duration (s) for each trial; (7) average (μV); duration (s) average and range for each type of exercise; (8) comments made by patient; (9) outputs of the swallowing detection and characterization algorithm 362; and (10) daily percent of trials completed from those prescribed, as a metric of adherence. These measurements can be communicated to the clinician at the end of each practice; as well, longitudinal analysis over multiple sessions can enable assessment of patient progress over time.

In some embodiments, at the start of every session, a calibration step can take place where rest and normal swallows are recorded. The software can then calculate the average and range signal amplitude across an initial number of normal swallows. In some embodiments, this initial calibration step can yield the daily targets for the practice following. In some embodiments, the training software can be gamified, meaning that game concepts and design can be used to engage patients and achieve maximal effort. In some embodiments, game concepts can comprise realistic graphics instead of childish ones, levels denoting progress to singular tasks, and feedback relevant to swallowing rather than to the game goals. In some embodiments, swallowing diagnosis and treatment application 316 comprise practice reminders and progress bars as goal setting.

In some embodiments, the application can connect to the scheduler or notification section of computing device (300) and can further schedule an alarm, notification or message to trigger on their device when the patient is to do their exercises. In some embodiments, the alarm, message or notification can be scheduled using an external device, server or third party service to provide the trigger for the patient to do their exercises.

In some embodiments, swallowing diagnosis and treatment application 316 can comprise a fishing game where the depth travelled by the lure is contingent on the duration of submental muscle contraction at or above 30% of the daily target amplitude. The longer the contraction, the deeper the lure travels and the more fish the player is likely to catch. In some embodiments, swallowing diagnosis and treatment application 316 can comprise providing feedback based on auditory or visual stimulus that gets more intense as the patient exerts energy to complete the exercise and then returns to a steady state when the patient completes the exercise. The intensity of this stimulus can be proportional to the intensity of the patient's exertion. In some embodiments, swallowing diagnosis and treatment application 316 can use various aspects of the feedback data to accomplish a progressive task that builds on the last task or on many of the tasks before it to provide an interesting experience for the user.

In some embodiments, swallowing diagnosis and treatment application 316 can calibrate the practice targets according to the patient's daily swallowing ability, thereby avoiding frustration if an arbitrary target is not met. Further, in some embodiments, patients can practice with regular swallows if swallowing exercises are too difficult or contraindicated. In some embodiments, trials can be summarized at the end of practice, displayed and compared to previous sessions. This way, the patient can receive quick feedback on whether or not he/she is improving in their practice. In some embodiments, swallowing diagnosis and treatment application 316 can walk patients through device set-up, thereby providing another level of assurance. Further, a clinician may spend the first therapy session in the clinic, training the patient on the use of the device and application, prior to home treatment. The clinician then will remotely-monitor home practice.

In some embodiments, the functions described can be implemented in hardware, software, firmware or any combination thereof as well known to those skilled in the art. If implemented in software, the functions can be stored on, or transmitted over, as one or more instructions or code, a computer-readable medium and executed by a hardware-based processing unit. In some embodiments, computer-readable media can comprise computer-readable storage media, which corresponds to a tangible medium such as data storage media or communication media including any medium that facilitates transfer of a computer program from one place to another, e.g., according to a communication protocol as well known to those skilled in the art. In this manner, computer-readable media generally can correspond to: (1) tangible computer-readable storage media which is non-transitory; or (2) a communication medium such as a signal or carrier wave. Data storage media can comprise any available media that can be accessed by one or more computers or one or more processors to retrieve instructions, code and/or data structures for implementation of the techniques described in this disclosure as well known to those skilled in the art. A computer program product can comprise a computer-readable medium.

By way of example, and not limitation, in some embodiments, such computer-readable storage media can comprise RAM, ROM, EEPROM, CD-ROM or other optical disk storage, magnetic disk storage, or other magnetic storage devices, flash memory or any other medium that can be used to store desired program code in the form of instructions or data structures and that can be accessed by a computer as well known to those skilled in the art. Also, any connection can be properly termed a computer-readable medium. In some embodiments, if instructions are transmitted from a website, server, or other remote source using a coaxial cable, fiber optic cable, twisted pair, digital subscriber line ("DSL") or wireless technologies such as infrared, radio, and microwave, then the coaxial cable, fiber optic cable, twisted pair, DSL, or wireless technologies such as infrared, radio, and microwave can be included in the definition of medium. It should be understood, however, that computer-readable storage media and data storage media do not include connections, carrier waves, signals, or other transient media, but are instead directed to non-transient, tangible storage media. Disk and disc, as used herein, includes compact disc ("CD"), laser disc, optical disc, digital versatile disc ("DVD"), floppy disk and Blu-ray disc, where disks usually reproduce data magnetically, while discs reproduce data optically with lasers. Combinations of the above should also be included within the scope of computer-readable media.

In some embodiments, instructions can be executed by one or more processors, such as one or more digital signal processors ("DSPs"), general purpose microprocessors, application specific integrated circuits ("ASICs"), field programmable logic arrays ("FPGAs") or other equivalent integrated or discrete logic circuitry as well known to those skilled in the art. Accordingly, the term "processor," as used herein can refer to any of the foregoing structure or any other structure suitable for implementation of the techniques described herein. In addition, in some embodiments, the functionality described herein can be provided within dedicated hardware and/or software modules as well known to those skilled in the art. Also, the techniques can be fully implemented in one or more circuits or logic elements.

In some embodiments, the techniques of this disclosure can be implemented in a wide variety of devices or apparatuses, including a wireless handset, an integrated circuit ("IC") or a set of ICs (e.g., a chip set). Various components, modules or units as described in this disclosure emphasize functional aspects of devices configured to perform the disclosed techniques, but do not necessarily require realization by different hardware units. Rather, as described above, various units can be combined in a codec hardware unit or can be provided by a collection of inter-operative hardware units, including one or more processors as described above, in conjunction with suitable software and/or firmware as well known to those skilled in the art.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

What is claimed is:

1. A system for use in the diagnosis and treatment of a swallowing disorder of a patient, the system comprising:
   a) a first computing device;
   b) a measurement device configured for attaching to the patient, the measurement device operatively coupled to a second computing device, wherein the second computing device is configured to transmit surface electromyography ("sEMG") data generated by the patient as the patient swallows to the first computing device, and wherein the measurement device further comprises a chin attachment configured for attachment to a chin of the patient, the chin attachment further comprising at least one sensor configured to collect the sEMG data from the patient; and
   c) an analysis module disposed in the first computing device, the analysis module configured to analyze the sEMG data and provide an output to a game module disposed in the first computing device, wherein the game module is configured to use said output to achieve functions associated with a game as the patient engages in swallowing exercises, wherein said functions include a function that provides, during the swallowing exercises, sensory feedback initiated at the first computing device, having an intensity proportional to the patient's exertion level, wherein exertion targets for the swallowing exercise include target signal amplitudes set based on a self-calibration that estimates the patient's ability using signal amplitudes of collected sEMG data, and wherein the sensory feedback changes over a course of the exercise in dependence on a duration that the patient maintains a submental muscle contraction at or above the target signal amplitude, and the change in sensory feedback is configured to encourage the patient to prolong the duration.

2. The system as set forth in claim 1, wherein the chin attachment comprises a housing, the housing comprising first and second housing halves configured to releasably attach together, and wherein the measurement device and the second computing device are disposed in the housing.

3. The system as set forth in claim 2, wherein the second computing device further comprises a wireless transceiver module, a battery, and a printed circuit board connected to the at least one sensor.

4. The system as set forth in claim 1, wherein the second computing device is configured for amplifying and filtering an sEMG signal derived from the sEMG data.

5. The system as set forth in claim 4, wherein the second computing device is configured for transmitting the sEMG signal to the first computing device.

6. The system as set forth in claim 5, wherein the first computing device comprises one or more processors configured for:
   a) receiving the sEMG data from the sEMG signal; and
   b) generating a graphical user interface based on the received sEMG data.

7. The system as set forth in claim 6, wherein the graphical user interface IS configured for indicating the duration of submental muscle contraction in the patient.

8. The system as set forth in claim 5, wherein the first computing device comprises one or more processors configured for:
   a) receiving the sEMG data from the sEMG signal; and
   b) calculating an average and a range signal amplitude of the sEMG data during a calibration phase.

9. The system as set forth in claim 1, wherein the first computing device comprises one or more processors configured for determining one or more of a group consisting of: time of log-in, duration of session, length of time since last session, session's target amplitude, type of exercise practiced, number of trials, amplitude for each trial, duration for each trial, average for each type of exercise, duration average for each type of exercise, and range for each type of exercise.

10. The system as set forth in claim 1, wherein the analysis module is configured to detect swallowing characteristics of the patient.

11. The system as set forth in claim 1, further comprising a calibration module disposed in the first computing device, the calibration module configured to achieve functions associated with a warm-up phase and a self-calibration phase of the system.

12. The system as set forth in claim 1, wherein said sensory feedback includes at least one of audible feedback or visual feedback.

13. The system as set forth in claim 1, wherein the self-calibration estimates the patient's ability for a particular day to set at least one of the exertion targets for the swallowing exercises of the particular day.

14. The system as set forth in claim 1, wherein the self-calibration estimates the patient's ability for a particular exercise session to set at least one of the exertion targets for the swallowing exercises of the particular exercise session.

15. A method for use in the diagnosis and treatment of a swallowing disorder of a patient, the method comprising the steps of:

a) receiving a system, comprising:
   i) a first computing device,
   ii) a measurement device configured for attaching to the patient, the measurement device operatively coupled to a second computing device, wherein the second computing device is configured to transmit surface electromyography ("sEMG") data generated by the patient as the patient swallows to the first computing device, and wherein the measurement device further comprises a chin attachment configured for attachment to a chin of the patient, the chin attachment further comprising at least one sensor configured to collect the sEMG data from the patient, and
   iii) an analysis module disposed in the first computing device, the analysis module configured to analyze the sEMG data and provide an output to a game module disposed in the first computing device, wherein the game module is configured to use said output to achieve functions associated with a game as the patient engages in swallowing exercises, wherein said functions include a function that provides, during the swallowing exercises, sensory feedback initiated at the first computing device, having an intensity proportional to the patient's exertion level, wherein exertion targets for the swallowing exercise include target signal amplitudes set based on a self-calibration that estimates the patient's ability using signal amplitudes of collected sEMG data, and wherein the sensory feedback changes over a course of the exercise in dependence on a duration that the patient maintains a submental muscle contraction at or above the target signal amplitude, and the change in sensory feedback is configured to encourage the patient to prolong the duration;
b) attaching the measurement device to a chin of the patient, and
c) using the sEMG data to measure muscle contraction of the patient when the patient swallows.

16. The method as set forth in claim 15, wherein said sensory feedback includes at least one of audible feedback or visual feedback to the patient, and wherein the feedback provides an indication of the muscle contraction to the patient.

17. The method as set forth in claim 15, whereby the method is used in the diagnosis of a swallowing disorder of a patient.

18. The method as set forth in claim 15, whereby the method is used in the treatment of a swallowing disorder of a patient.

19. The method as set forth in claim 15, wherein the chin attachment comprises a housing, the housing comprising first and second housing halves configured to releasably attach together, and wherein the measurement device and the second computing device are disposed in the housing.

20. The method as set forth in claim 15, wherein the second computing device further comprises a wireless transceiver module, a battery, and a printed circuit board connected to the at least one sensor.

21. The method as set forth in claim 15, further comprising amplifying and filtering an sEMG signal derived from the sEMG data with the second computing device.

22. The method as set forth in claim 21, further comprising transmitting the sEMG signal to the first computing device.

23. The method as set forth in claim 22, further comprising, using the first computing device:
a) receiving the sEMG; and
b) generating a graphical user interface based on the received sEMG signal.

24. The method as set forth in claim 23, further comprising indicating the duration of submental muscle contraction in the patient using the first computing device.

25. The method as set forth in claim 22, further comprising, using the first computing device:
a) receiving the sEMG signal; and
b) calculating an average and a range signal amplitude of the sEMG signal during a calibration phase.

26. The method as set forth in claim 15, further comprising using the first computing device to determine one or more of a group consisting of: time of log-in, duration of session, length of time since last session, session's target amplitude, type of exercise practiced, number of trials, amplitude for each trial, duration for each trial, average for each type of exercise, duration average for each type of exercise, and range for each type of exercise.

27. The method as set forth in claim 15, further comprising controlling the functions of the game using the sEMG data generated by the patient engaging in the swallowing exercises.

28. The method as set forth in claim 15, further comprising detecting swallowing characteristics of the patient using the analysis module.

29. The method as set forth in claim 15, further comprising calibrating the system using a calibration module disposed in the first computing device, the calibration module configured to achieve functions associated with a warm-up phase and a self-calibration phase of the system.

30. A method of providing sensory feedback during a swallowing exercise, the method comprising:
setting an exertion target, for a user performing the swallowing exercise, based on a self-calibration that estimates the user's ability using signal amplitudes of surface electromyography (sEMG) data, wherein the exertion target includes a target signal amplitude of muscle contractions to be reached during the swallowing exercise;
receiving sEMG data from a measurement device attached to the user's chin as the user swallows while performing the swallowing exercise; and
upon processing the sEMG data, generating sensory feedback at a computing device operated by the user, wherein the sensory feedback has an intensity proportional to the user's exertion level as the user performs the swallowing exercise, and wherein the sensory feedback changes over a course of the exercise in dependence on a duration that the user maintains a submental muscle contraction at or above the target signal amplitude, and the change in sensory feedback is configured to encourage the user to prolong the duration.

31. The method of claim 30, wherein the sensory feedback is responsive to the duration that a muscle contraction is maintained at or above a pre-defined quantum higher than the target signal amplitude.

* * * * *